(12) United States Patent
Nakane et al.

(10) Patent No.: US 11,321,841 B2
(45) Date of Patent: May 3, 2022

(54) IMAGE ANALYSIS METHOD, IMAGE ANALYSIS DEVICE, IMAGE ANALYSIS SYSTEM, AND STORAGE MEDIUM

(71) Applicant: OSAKA UNIVERSITY, Osaka (JP)

(72) Inventors: Kazuaki Nakane, Osaka (JP); Hirofumi Yamamoto, Osaka (JP); Mizuho Nishio, Kyoto (JP)

(73) Assignee: OSAKA UNIVERSITY, Osaka (JP)

( * ) Notice: Subject to any disclaimer, the term of this patent is extended or adjusted under 35 U.S.C. 154(b) by 69 days.

(21) Appl. No.: 16/766,333

(22) PCT Filed: Nov. 5, 2018

(86) PCT No.: PCT/JP2018/040977
§ 371 (c)(1),
(2) Date: May 22, 2020

(87) PCT Pub. No.: WO2019/102829
PCT Pub. Date: May 31, 2019

(65) Prior Publication Data
US 2020/0372649 A1    Nov. 26, 2020

(30) Foreign Application Priority Data

Nov. 24, 2017 (JP) .............................. JP2017-226260

(51) Int. Cl.
*G06T 7/00* (2017.01)
*G06T 7/187* (2017.01)
(Continued)

(52) U.S. Cl.
CPC .............. *G06T 7/0014* (2013.01); *G06T 7/11* (2017.01); *G06T 7/136* (2017.01); *G06T 7/187* (2017.01);
(Continued)

(58) Field of Classification Search
CPC ...... G06K 9/00147; G06T 2207/30024; G06T 2207/30096; G06T 7/0012; G06T 7/12; G06T 7/187; G06T 7/62
See application file for complete search history.

(56) References Cited

U.S. PATENT DOCUMENTS

| | | | |
|---|---|---|---|
| 8,718,377 B2 * | 5/2014 | Suzuki | G06T 7/187 |
| | | | 382/128 |
| 2007/0036434 A1 * | 2/2007 | Saveliev | G06V 10/42 |
| | | | 382/173 |

(Continued)

FOREIGN PATENT DOCUMENTS

WO    2010087112 A1    8/2010

OTHER PUBLICATIONS

M. Nishio et al., "Automated prediction of emphysema visual score using homology-based quantification of low-attenuation lung region", May 2017, PLoS One 12(5), p. 1-12, (Year: 2017).*

(Continued)

*Primary Examiner* — Gandhi Thirugnanam
(74) *Attorney, Agent, or Firm* — Kagan Binder, PLLC

(57) ABSTRACT

In order to assess, with high accuracy, a degree of a change having occurred in a structure, the present invention includes: a Betti number calculating section (42) configured to (I) generate, with respect to a single captured image obtained by capturing an image of a structure, a plurality of binarized images having respective binarization reference values different from each other and (II) calculate, for each of the plurality of binarized images, a first characteristic numerical value indicative of the number of connected regions each of which is obtained by connecting pixels each having one of pixel values obtained by binarization; and a prediction score determining section (44) configured to determine, in accordance with a result of a comparison, information on a change having occurred in the structure, the (Continued)

comparison having been made between (i) a pattern indicative of a relationship between (a) the respective binarization reference values and (b) the first characteristic numerical value and (ii) a predetermined reference pattern.

11 Claims, 10 Drawing Sheets

(51) Int. Cl.
  *G06T 7/136* (2017.01)
  *G06T 7/11* (2017.01)
  *A61B 5/00* (2006.01)
  *A61B 6/03* (2006.01)
(52) U.S. Cl.
  CPC ........... *A61B 5/7264* (2013.01); *A61B 5/7275* (2013.01); *A61B 6/032* (2013.01); *G06T 2207/10081* (2013.01); *G06T 2207/20081* (2013.01); *G06T 2207/30061* (2013.01); *G06T 2207/30096* (2013.01)

(56) References Cited

U.S. PATENT DOCUMENTS

| | | | | |
|---|---|---|---|---|
| 2011/0274340 | A1* | 11/2011 | Suzuki | G06V 20/698 382/133 |
| 2017/0147946 | A1* | 5/2017 | Umeda | G06N 5/046 |
| 2018/0204324 | A1* | 7/2018 | Kawaguchi | G01N 21/84 |
| 2020/0372649 | A1* | 11/2020 | Nakane | G06T 7/11 |

OTHER PUBLICATIONS

International Search Report for International Application No. PCT/JP2018/040977, dated Jan. 29, 2019 (4 pages).
Wille et al., "Visual assessment of early emphysema and interstitial abnormalities on CT is useful in lung cancer risk analysis", European Radiology, vol. 26, pp. 487-494, 2016 (8 pages).
Smith et al., "Emphysema detected on computed tomography and risk of lung cancer: A systematic review and meta-analysis", Lung Cancer, vol. 77, pp. 58-63, 2012, (4 pages).
Nishio et al., "Regarding Relationship between Quantitative and Visual Evaluation of Emphysema by Homology and Visual Evaluation and Prediction of Visual Evaluation by Machine Learning", Preprints of 9th Japanese Society of Pulmonary Functional Imaging, p. 66, 2017, Non-Official Translation, (3 pages).
Nakane et al., "Tissue Image Analysis Method via Homology Concept", Division of Health Sciences, vol. 35, No. 5, pp. 86-91, 2017, Non-Official Translation, (13 pages).
Nakane, "About Automation of Cancer Pathological Image Diagnosis", Department of Health Sciences, Graduate School of Medicine, vol. 1917, pp. 37-42, 2014, Non-Official Translation, (14 pages).
Qaiser et al., "Persistent Homology for Fast Tumor Segmentation in Whole Slide Histology Images", Procedia Computer Science, vol. 90, pp. 119-124, 2016, (6 pages).
Nakane et al., "Homology-based method for detecting regions of interest in colonic digital images", Diagnostic Pathology, 10:36, pp. 1-5, 2015, (5 pages).
Nakane et al., "The image analyzing method based on the homology concept", Retrieved from https://kaken.nii.ac.jp/file/KAKENHI-PROJECT-26310209/26310209seika.pdf, on Jan. 15, 2019, Research performance report on Grants-in-Aid for Scientific Research of Ministry of Education, Culture, Sports, Science and Technology, Institution, No. 14401, Project No. 26310209, (5 pages).
Nishio et al., "Application of the homology method for quantification of low-attenuation lung region in patients with and without COPD", International Journal of COPD, vol. 11, pp. 2125-2137, 2016, (13 pages).
Nishio et al., "Automated prediction of emphysema visual score using homology-based quantification of low-attenuation lung region", vol. 12, No. 5, pp. 1-12, 2017, (12 pages).
International Report on Patentability for International Application No. PCT/JP2018/040977, dated Jun. 4, 2020 (8 pages).

\* cited by examiner

| PREDICTION METHOD | p VALUE IN t-TEST OF RESULT OF PREDICTION OF PRESENCE OF LUNG CANCER |
|---|---|
| BRINKMAN INDEX (SMOKING HISTORY) | 0.0243 |
| LUNG REGION | 0.276 |
| LAA% (−950 HU) | 0.312 |
| LAA% (−910 HU) | 0.128 |
| LAA% (−880 HU) | 0.0648 |
| $b_0$ (−880 HU) | 0.042 |
| $b_1$ (−880 HU) | 0.00511 |

FIG. 11

| MODEL | PREDICTOR VARIABLE | COEFFICIENT | STANDARD ERROR | p VALUE | AIC |
|---|---|---|---|---|---|
| MODEL IN WHICH BASIC INDEXES WERE USED | MALE | −0.347 | 0.208 | 0.0959 | 785.9 |
| | AGE | 0.0258 | 0.00731 | 0.000414 | |
| | SMOKING HISTORY | 0.000281 | 0.000128 | 0.0283 | |
| MODEL IN WHICH LAA% IN ADDITION TO BASIC INDEXES WAS USED AS INDEX | MALE | −0.379 | 0.21 | 0.071 | 786.2 |
| | AGE | 0.0248 | 0.00737 | 0.000758 | |
| | SMOKING HISTORY | 0.000273 | 0.000128 | 0.0332 | |
| | LAA% (−880 HU) | 0.00835 | 0.00649 | 0.199 | |
| MODEL IN WHICH BETTI NUMBER IN ADDITION TO BASIC INDEXES WAS USED AS INDEX | MALE | −0.438 | 0.212 | 0.0393 | 779.8 |
| | AGE | 0.026 | 0.00743 | 0.000479 | |
| | SMOKING HISTORY | 0.000294 | 0.00013 | 0.0238 | |
| | $b_1$ (−880 HU) | 0.000104 | 0.000037 | 0.00487 | |

IMAGE ANALYSIS METHOD, IMAGE ANALYSIS DEVICE, IMAGE ANALYSIS SYSTEM, AND STORAGE MEDIUM

CROSS-REFERENCE TO RELATED APPLICATIONS

This application claims priority to International Application No. PCT/JP2018/040977, filed Nov. 5, 2018 and titled "IMAGE ANALYSIS METHOD, IMAGE ANALYSIS DEVICE, IMAGE ANALYSIS SYSTEM, IMAGE ANALYSIS PROGRAM, AND STORAGE MEDIUM," which in turn claims priority from a Japanese Patent Application having serial number 2017-226260, filed Nov. 24, 2017, titled "IMAGE ANALYSIS METHOD, IMAGE ANALYSIS DEVICE, IMAGE ANALYSIS SYSTEM, IMAGE ANALYSIS PROGRAM, AND STORAGE MEDIUM," both of which are incorporated herein by reference in their entireties.

TECHNICAL FIELD

The present invention relates to an image analyzing method and an image analyzing device each of which is for (i) analyzing an image obtained by capturing an image of a structure and (ii) outputting information in accordance with which to assess a degree of a change having occurred in a structure.

BACKGROUND ART

Computed tomography (CT) is a technique essential in carrying out a medical image diagnosis. Examples of an organ for which an image diagnosis carried out with use of a CT image is mainly employed include a lung. A chest CT image obtained by capturing an image of the chest of a subject is used to diagnose a disease having developed in a lung.

A diagnosis is conventionally visually carried out by, for example, a doctor. Note, however, that a diagnosis based on a result of an analysis of a chest CT image has been carried out in recent years. For example, screening of a lung CT image (i) makes it possible to find and diagnose, for example, chronic obstructive pulmonary disease ((COPD), hereinafter abbreviated as "COPD") in an early stage and carry out a treatment with respect to such a disease and (ii) is a technique that is important in maintaining healthy life expectancy not only in Japan but also in the entire world.

Examples of a quantitative index that is used to diagnose, by an image analysis of a chest CT image, lesions having developed in a lung, such as COPD, pulmonary emphysema, and lung cancer include LAA %. In an image diagnosis carried out with use of LAA %, a proportion of a low-attenuation lung area, which is a region in which an X-ray absorption rate is low (a CT value is not more than −950 HU), to three regions of a lung, which regions are captured in a chest CT image and are an upper part, a middle part, and a lower part, respectively, is used as an index.

Pulmonary emphysema refers to a condition in which an alveolus is expanded, an alveolus wall that absorbs an X-ray disappears after its atrophy, and a lung is continuously extended. Thus, in a lung CT image, a region in which pulmonary emphysema has developed is shown darker as compared with a normal lung region. In a case where LAA % is employed, for example, regions of a lung which regions are captured in a chest CT image are extracted and binarized by using a CT value of, for example, −950 HU as a threshold. A proportion (%) of a pixel number of a low-attenuation lung area (i.e., a region in which a pixel value of 0 has been obtained as a result of binarization) to a total pixel number of the regions of the lung is calculated. This proportion is known as a value that is correlative with the severity of pulmonary emphysema.

A radiologist, a doctor of respiratory medicine, and the like who each diagnose a lung CT image point out that pulmonary emphysema is a risk factor of lung cancer. As described in Non-patent Literatures 1 and 2, it is effective to employ LAA % as a quantitative index for detection of pulmonary emphysema. Note, however, that LAA % frequently makes it impossible to accurately assess the severity of pulmonary emphysema. Thus, it is pointed out that it is difficult to assess a risk of development into lung cancer in accordance with determination of the severity of pulmonary emphysema with use of LAA %.

CITATION LIST

[Non-Patent Literatures]
[Non-Patent Literature 1]
Smith B M et al., "Emphysema detected on computed tomography and risk of lung cancer: a systematic review and meta-analysis" Lung Cancer, Vol. 77(1), p 58-63, 2012
[Non-patent Literature 2]
Wille M M W et al., "Visual assessment of early emphysema and interstitial abnormalities on CT is useful in lung cancer risk analysis" Ear Radial. Vol. 26(2), p 48'7-494, 2016

SUMMARY OF INVENTION

Technical Problem

An image analyzing technique has been demanded that makes it possible to assess a risk of development from pulmonary emphysema into lung cancer as a doctor is capable of assessing a risk of development from pulmonary emphysema into lung cancer by visually diagnosing a lung CT image.

In general, it is frequently important in an image diagnosis to assess a risk of canceration. Thus, it is important for an image analyzing technique to (i) understand a structural characteristic of a lesion having developed in a structure and (ii) provide information for use in determination of a possibility of development of the lesion into a severer disease. This applies not only to the case of an assessment of a risk of development from pulmonary emphysema into lung cancer, but also to the case of an assessment of a risk of development of a lesion into a severer disease of various organs and structures.

An aspect of the present invention has been made so as to solve the problem, and an object of an aspect of the present invention is to achieve, for example, an image analyzing method and an image analyzing device each of which is for outputting information for highly accurately assessing, as a doctor does, a degree of a change, having occurred in a structure, by analyzing an image of the structure.

Solution to Problem

In order to attain the object, an image analyzing method in accordance with an aspect of the present invention includes: a binarizing step of generating, from the captured image, a plurality of binarized images having respective binarization reference values different from each other; a calculation step of calculating, for each of the plurality of binarized images, a first characteristic numerical value indicative of the number of connected regions each of which is obtained by connecting pixels each having one of pixel values obtained by binarization; and a determination step of determining, in accordance with a result of a comparison, information on a change having occurred in the structure, the comparison having been made between (i) a first pattern indicative of a relationship between (a) the respective binarization reference values and (b) the first characteristic numerical value and (ii) a predetermined reference pattern.

An image analyzing device in accordance with an aspect of the present invention includes: a binarizing section configured to generate, from the captured image, a plurality of binarized images having respective binarization reference values different from each other; a calculation section configured to calculate, for each of the plurality of binarized images, a first characteristic numerical value indicative of the number of connected regions each of which is obtained by connecting pixels each having one of pixel values obtained by binarization; a comparison section configured to make a comparison between (i) a first pattern indicative of a relationship between (a) the respective binarization reference values and (b) the first characteristic numerical value and (ii) a predetermined reference pattern; and a determination section configured to determine, in accordance with a result of the comparison, information on a change having occurred in the structure.

An image analyzing system in accordance with an aspect of the present invention includes: an image analyzing device recited above; an external device configured to transmit, to the image analyzing device, image data indicative of a captured image; and a presenting device configured to (i) obtain information determined by the image analyzing device and (ii) present the information.

Advantageous Effects of Invention

An aspect of the present invention makes it possible to output information for highly accurately assessing, by analyzing an image of a structure, a degree of a change having occurred in the structure.

BRIEF DESCRIPTION OF DRAWINGS

FIG. 11 is a table showing a result of comparison between accuracies in prediction of lung cancer in a case where basic indexes that are an age, a sex, and a smoking history (Brinkman index) were used, in a case where LAA % in addition to the basic indexes was used as an index, and in a case where a Betti number in addition to the basic indexes was used as an index.

DESCRIPTION OF EMBODIMENTS

Embodiment 1

Figure 1:
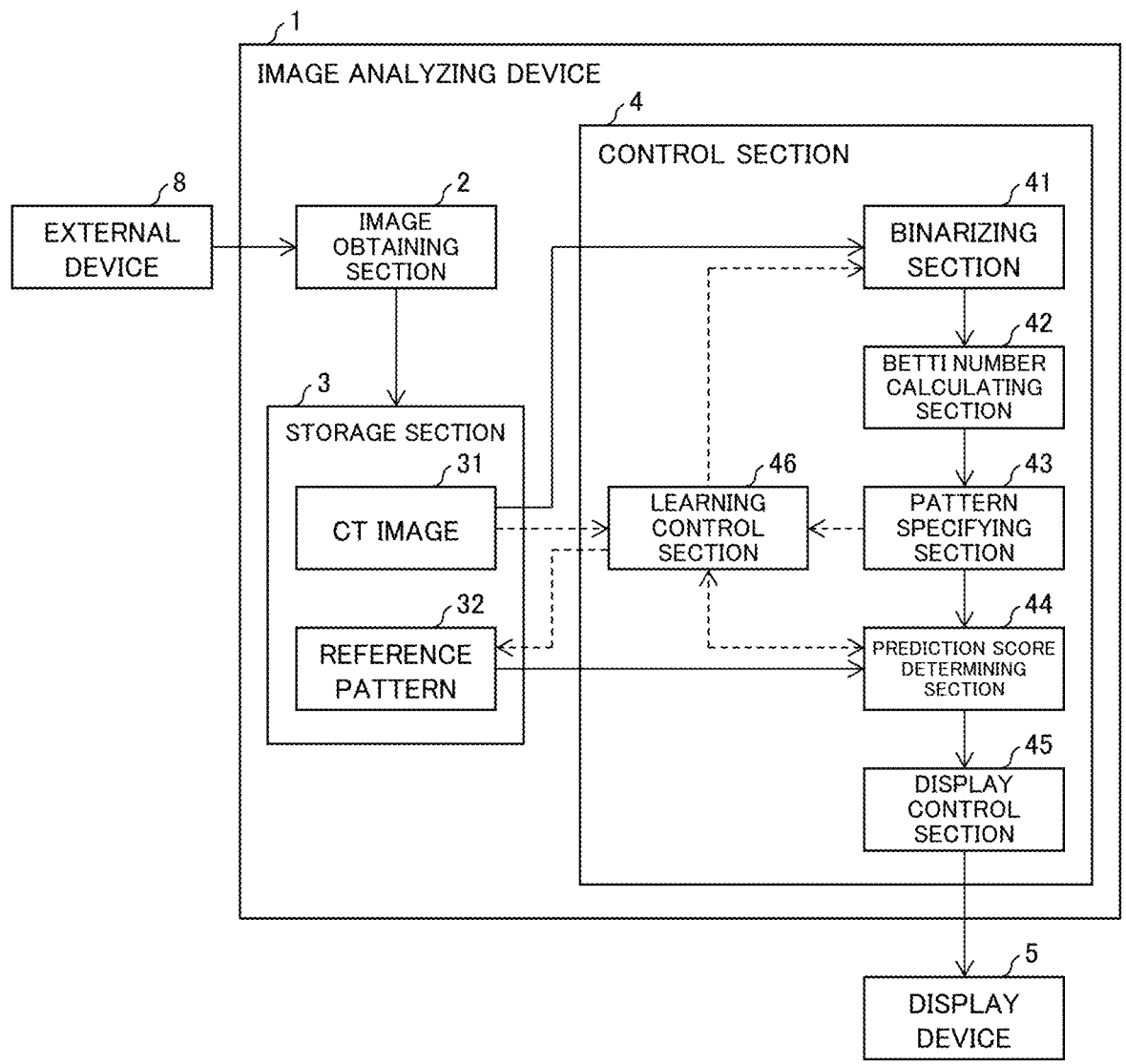
FIG. 1 is a functional block diagram illustrating a configuration example of an image analyzing device in accordance with Embodiment 1 of the present invention.

The following description will specifically discuss an embodiment of the present invention.

(Technical Idea on the Present Invention)

First, a technical idea on the present invention will be described below. An object of the present invention is to (i) analyze a captured image obtained by capturing an image of a structure and (ii) output information useful in highly accurately determining (a) presence of a lesion having developed in the structure that is shown in the captured image and (b) a possibility of canceration.

The inventors of the present invention checked a computed tomography (CT) image obtained by capturing an image of a chest of a subject, and carried out, in detail, a comparison and a study with respect to a relationship between the severity of pulmonary emphysema and a possibility of canceration. Specifically, a plurality of binarized images having respective binarization reference values different from each other were generated with respect to a region of a chest CT image in which region a lung was shown. Then, it was checked how a zero-dimensional Betti number ($b_0$, first characteristic numerical value) and a one-dimensional Betti number ($b_1$, second characteristic numerical value) change in accordance with the binarization reference values, the zero-dimensional Betti number and the one-dimensional Betti number each having been calculated for a lung CT image captured in each of the binarized images. As a result, it was found that in the lung CT image, it is possible to use, as an index for determining the severity of pulmonary emphysema and assessing a possibility of canceration, each of (i) a change in zero-dimensional Betti number which change is caused by a change in binarization reference value and (ii) a change in one-dimensional Betti number which change is caused by a change in binarization reference value.

An embodiment of the present invention can be configured to employ one of the zero-dimensional Betti number and the one-dimensional Betti number. Note, however, that the following description will discuss a case where both the zero-dimensional Betti number and the one-dimensional Betti number are employed. Use of both the zero-dimensional Betti number and the one-dimensional Betti number makes it possible to output more accurate information.

Note that a binarization reference value is herein set in accordance with a CT value of each pixel. Specifically, a binarization reference value is set to a CT value of −1000 HU to −700 HU, which is commonly set in a chest CT image whose image capturing target is a lung. For example, in a case where a binarization reference value is set to −900 HU, a pixel that has a CT value of not more than −900 HU has a pixel value of 0, and a pixel that has a CT value of more than −900 HU has a pixel value of 1.

The following description will discuss an example in which an image analyzing device 1 analyzes an X-ray CT image and outputs information useful for determination of the severity of pulmonary emphysema having developed in a lung. Note, however, that a structure to be analyzed in each embodiment of the present invention is not limited to a lung. Note also that an image to be analyzed in each embodiment of the present invention is not limited to an X-ray CT image. The image analyzing device 1 in accordance with an aspect of the present invention is applicable to any medical image. For example, the image analyzing device 1 in accordance with an aspect of the present invention is suitably applicable to an analysis of (1) images of, for example, a liver and a breast which images are captured in an X-ray examination (including mammography), (2) images of, for example, a brain and a pancreas which images are captured in a magnetic resonance imaging (MRI) scan, and (3) images captured in positron emission tomography (PET) and in a radioisotope (RI) examination (also called an isotope examination).

<Lung CT Image>

For example, in a lung CT image, a normal lung is shown as a blackish region over which a light milk-white haze hangs, whereas a region of a lung which region is affected with pulmonary emphysema is shown as a black region with a thin mist because an alveolus wall has disappeared after its atrophy.

It is commonly detected in a lung CT image at an early stage of destruction and fusion of alveoli that the alveoli destructed and fused are a low-attenuation lung area surrounded by a normal lung. There is frequently no clear wall at a boundary between a normal lung region and a low-attenuation lung area. Note, however, that low-attenuation areas each having a diameter of approximately 1 cm or so come to be scattered at an early stage of pulmonary emphysema. As pulmonary emphysema increases in severity, low-attenuation areas are fused to increase, whereas the normal lung region decreases.

A quantitative index such as LAA % is applicable to a diagnosis carried out, by an image analysis of a chest CT image, with respect to a lesion having developed in a lung, such as pulmonary emphysema. LAA % (i) is obtained by calculating a proportion (%) of a low-attenuation lung area to an entire lung region in a lung CT image and (ii) is used to determine the severity of pulmonary emphysema in accordance with the proportion. Note here that the severity means a degree of a change having occurred in a lung and refers to a degree of development of a lesion that is absent in a normal lung.

In a case where a doctor determines presence and the severity of pulmonary emphysema in accordance with a chest CT image, a visual score that is classified into a plurality of levels in accordance with the severity of pulmonary emphysema having developed in a captured lung is associated, as determined information, with the chest CT image.

The following description will take, as an example, a case where a visual score is applied, the visual score being classified, in accordance with the severity of pulmonary emphysema, into the following six levels: 0 indicating that no pulmonary emphysema is found; 1 indicating that the severity of pulmonary emphysema is low; 2 and 3 each indicating that the severity of pulmonary emphysema is moderate; and 4 and 5 each indicating that the severity of pulmonary emphysema is great.

Note that a visual score, which has several types, is not limited to the above visual score. For example, it is possible to alternatively use, in a lung CT image, a Goddard classification pulmonary emphysema score (maximum possible score: 24 points) that is classified by level in accordance with the severity of pulmonary emphysema by summating visual assessments (five levels ranging from 0 point to 4 points) of six regions.

<Mathematical Representation for Analysis of Lung CT Image>

The inventors of the present invention attempted to apply, to quantification of a change having occurred in a structure, a concept of homology, in particular, persistent homology. Homology is one of mathematical fields which facilitates an analysis of, for example, connection between figures by substituting an algebraic expression for morphological characteristics of the figures. In particular, the inventors of the present invention focused their attention on use of a zero-dimensional Betti number and a one-dimensional Betti number in a two-dimensional image among homology concepts.

The concept of homology is a mathematical concept indicative of connection and contact between constituents. In a pathological image, an appropriate binarization reference value (also referred to as a binarization parameter) is set so that the pathological image is binarized. Then, from the binarized image, a zero-dimensional Betti number and a one-dimensional Betti number per unit area of the binarized image are calculated. The zero-dimensional Betti number and the one-dimensional Betti number each having been thus calculated can be used to (i) assess a degree of connection between constituents of a structure shown in the pathological image and (ii) assess a degree of contact between the constituents.

A Betti number is a topological pointer number which is independent of a shape of each of figures (for example, corresponding to constituents of a structure) but is dependent on merely contact and separation between figures. In a case where a q-th singular homology group is finitely generated, the q-th singular homology group can be expressed by a direct sum of a free Abelian group and a finite Abelian group. A rank of the free Abelian group is called a "Betti number." In a case of two-dimensional images, a zero-dimensional Betti number indicates the number of connected components, and a one-dimensional Betti number indicates the number of spaces (hereinafter may be referred to as "case-shaped regions") each of which is surrounded by a connected component(s). Specifically, the number of case-shaped regions indicates the number of "holes" formed by the connected component(s).

<Zero-Dimensional Betti Number>

A zero-dimensional Betti number is mathematically defined as follows. The number of connected components of a figure (also called a "one-dimensional complex") K obtained by a finite number of line segments is commonly referred to as a zero-dimensional Betti number. The expression "a figure obtained by connecting a finite number of points by a finite number of line segments is a connection" means that it is possible to reach any second vertex from any first vertex of the figure by following a side of the figure.

In each of a plurality of binarized images generated with respect to a lung CT image with use of different binarization reference values, the number of connected regions obtained by connecting pixels each having one of pixel values obtained by binarization (e.g., a pixel value of 0 obtained as a result of binarization) is a zero-dimensional Betti number. Thus, the zero-dimensional Betti number can be said to correspond to the number of low-attenuation lung areas in a lung CT image.

<One-Dimensional Betti Number>

A one-dimensional Betti number is mathematically defined as follows. A one-dimensional Betti number of the figure K is "r" in a case where the following conditions (1) and (2) are satisfied. (1) The number of connected components of the figure K remains unchanged even in a case where any r one-dimensional simplices (e.g., line segments), each of which is opened (does not have both ends), are removed from the figure (a connected one-dimensional complex) K obtained by connecting a finite number of line segments. (2) The figure K is not a connection (i.e., the number of connected components of the figure K is increased by one (1)) in a case where any (r+1) one-dimensional simplices, each of which is opened, are removed from the figure K.

In each of a plurality of binarized images generated with respect to a lung CT image with use of different binarization reference values, the number of case-shaped regions each of which is surrounded by pixels each having one of pixel values obtained by binarization (e.g., a pixel value of 0 obtained as a result of binarization) is a one-dimensional Betti number. Thus, the one-dimensional Betti number can be said to correspond to the number of normal lung regions in a lung CT image each of which regions is surrounded by a low-attenuation lung area(s).

(Overview of Image Analyzing Method)

Figure 2:
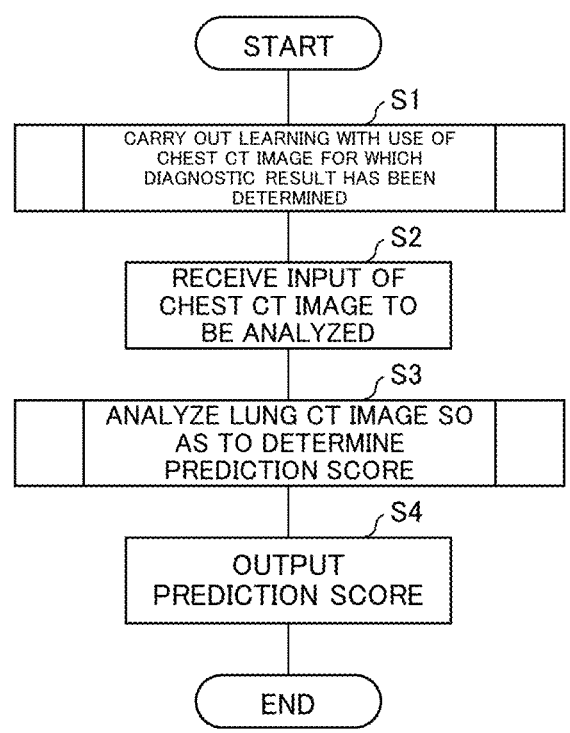
FIG. 2 is a flowchart illustrating an example of how a process of an image analyzing method in accordance with an aspect of the present invention is carried out.

First, an image analyzing method in accordance with an aspect of the present invention is a method for (i) analyzing a captured image obtained by capturing an image of a subject and (ii) determining and outputting information on a change having occurred in a structure captured. The following description will discuss an overview of the image analyzing method in accordance with an aspect of the present invention with use of FIG. 2. FIG. 2 is a flowchart illustrating an example of how a process of the image analyzing method in accordance with an aspect of the present invention is carried out. The following description will take, as an example, a process, carried out, by the image analyzing device 1, for analyzing a chest CT image of a subject and outputting information on the severity of, for example, pulmonary emphysema.

The following description will discuss a configuration in which a zero-dimensional Betti number and a one-dimensional Betti number are calculated. Note, however, that an aspect of the present invention can be alternatively configured such that only one of a zero-dimensional Betti number and a one-dimensional Betti number is calculated and used. However, since characteristics of a change having occurred in a structure are diverse and characteristics exhibited in a captured image are also diverse, an aspect of the present invention is desirably configured such that a zero-dimensional Betti number and a one-dimensional Betti number are calculated. This is because a configuration in which not only it is detected that a change having occurred in a structure is a change in number of connected regions of a captured image but also it is detected that a change having occurred in a structure is a change in number of case-shaped regions makes it possible to determine a more accurate prediction score.

First, machine learning is carried out with use of a chest CT image (i) that has been obtained by capturing an image of a subject who was examined by, for example, a doctor in the past and (ii) in accordance with which the severity of pulmonary emphysema and a risk of development from pulmonary emphysema into lung cancer have already been assessed by, for example, a doctor (step S1). In step S1, the chest CT image that has been obtained by capturing an image of a subject who was examined in the past is analyzed as in the case of an analysis carried out in step S3 with respect to a CT image to be analyzed. Then, a correlation between (a) a characteristic amount obtained by analyzing a lung CT image and (b) a visual score that has already been determined is learned. Note here that examples of a characteristic amount include (i) a numerical value indicative of a change in each of zero-dimensional Betti number and one-dimensional Betti number in accordance with a binarization reference value that is used to binarize the CT image, (ii) an increasing and decreasing pattern shown in a graph obtained by plotting such a change, and (iii) a coefficient value of a function approximately expressing such a graph.

Note that a case where it is determined that a visual score of pulmonary emphysema is a prediction score is herein described as an example. Note, however, that the scope of application of the present invention is not limited to determination of a visual score. For example, it is possible to learn a correlation between (a) a characteristic amount obtained by analyzing a tomographic image obtained with use of, for example, CT, MRI, PET, or RI and (b) any clinically significant index of a lesion which index has already been determined. Examples of the any clinically significant index include a risk of canceration, the severity of cancer (e.g., staging such as TNM staging), and a prognosis of cancer. By carrying out such learning, the image analyzing device 1 can analyze an image of a subject and output information on any clinically significant index.

Note here that a "prediction score" is an index (score) that is determined by a doctor and follows a visual score. The "prediction score" is a score that is obtained as a result of an analysis of a lung CT image and can be used to assess the severity of pulmonary emphysema and a risk of development from pulmonary emphysema into lung cancer. A specific process of step S1 will be described later by taking a specific example (see FIG. 3).

Next, a chest CT image of a subject is inputted (step S2).

Subsequently, the chest CT image inputted is analyzed so that a prediction score that can be used to assess the severity of pulmonary emphysema and a risk of development from pulmonary emphysema into lung cancer is determined (step S3). A specific process of step S3 will be described later by taking a specific example (see FIG. 7).

Finally, the prediction score determined in step S3 is outputted (step S4). An aspect in which the prediction score is outputted is not limited to any particular aspect provided that the prediction score is outputted so as to be presented to a user who wishes to use the prediction score. For example, the prediction score can be displayed in a display device 5, or can be outputted to a printer (not illustrated) or over a loudspeaker (not illustrated).

(Configuration of Image Analyzing Device 1)

Next, the following description will discuss, with reference to FIG. 1, a configuration of the image analyzing device 1 that allows the image analyzing method illustrated in FIG.

2 to be carried out. FIG. 1 is a block diagram illustrating an example of a configuration of the image analyzing device 1 in accordance with Embodiment 1 of the present invention. In FIG. 1, data flows related to step S1 of FIG. 2 are shown with broken lines, and data flows related to steps S2 to S4 of FIG. 2 are shown with solid lines.

As illustrated in FIG. 1, the image analyzing device 1 includes an image obtaining section 2 (receiving section), a storage section 3, and a control section 4. The storage section 3 stores therein at least CT images 31 and at least one reference pattern 32.

FIG. 1 illustrates an example in which the image analyzing device 1 is connected to the display device 5 (presenting section) that is provided separately from the image analyzing device 1. Note, however, that a configuration of the image analyzing device 1 is not limited to such a configuration. For example, the image analyzing device 1 can be configured so as to include therein the display device 5 (presenting section). Alternatively, the image analyzing device 1 can be configured so as to be connected to a plurality of display devices 5 by wire or wireless.

The image obtaining section 2 (i) obtains, from an external device 8, a captured image obtained by capturing an image of a structure (hereinafter referred to as a "CT image") and (ii) stores, in the storage section 3, the CT image thus obtained. Alternatively, the image obtaining section 2 can supply the CT image to a binarizing section 41. Note that examples of the external device 8 include (i) a personal computer that is connected to a CT device and (ii) a storage device in which image data can be stored. In a case where a structure to be analyzed is a lung, the CT image is a CT image obtained by capturing an image of a chest of a subject with an appropriate contrast. For example, a contrast of a CT image can be set as appropriate in accordance with an X-ray absorption rate of a structure to be analyzed.

In a case where the image analyzing device 1 diagnoses COPD in accordance with a lung CT image, the image obtaining section 2 desirably obtains a set of at least three chest CT images each including respective cross sections of an upper part, a middle part, and a lower part of a lung.

The image obtaining section 2 (i) obtains a combination of (a) a CT image that has been determined by a doctor and with which a visual score of a structure is associated as determined information in advance and (b) the visual score and (ii) stores the combination in the storage section 3. The CT image with which the visual score (determined information) is associated in advance is used as learning data to be inputted in machine learning carried out by a prediction score determining section 44.

The storage section 3 stores therein (1) the CT images 31 that have been obtained by the image obtaining section 2, (2) the at least one reference pattern 32 that has been generated in step S1 of FIG. 2, (3) a control program, executed by the control section 4, for controlling each section, (4) an OS program, (5) an application program, and (6) various sets of data that are read out in a case where the control section 4 executes the programs. The storage section 3 is constituted by a nonvolatile storage device such as a hard disk or a flash memory. Note that the image analyzing device 1 can include not only the storage section 3 but also a storage device that (i) is used as a working area in which data is temporarily stored while the programs are being executed and (ii) is exemplified by a volatile storage device such as a random access memory (RAM).

The display device 5 is a display device that displays, for example, output information outputted by the control section 4. Examples of the display device 5 include a liquid crystal display device. Note that the image analyzing device 1 can be configured to include a dedicated display device 5. Note also that the display device 5 can be configured such that a touch sensor is provided on a display screen of the display device 5 so that the display device 5 detects a touch operation carried out, by a user, with respect to a surface of the display screen.

(Configuration of Control Section 4)

The control section 4 analyzes a CT image obtained by the image obtaining section 2, and then outputs information indicative of the severity of COPD (e.g., pulmonary emphysema) captured in the CT image. The image analyzing section 4 further includes the binarizing section 41 (binarizing section, region extracting section), a Betti number calculating section 42 (calculation section), a pattern specifying section 43, the prediction score determining section 44 (comparison section, determination section), a display control section 45, and a learning control section 46.

From a chest CT image obtained by the image obtaining section 2, the binarizing section 41 cuts out (extracts), as a lung CT image, a region corresponding to a lung of a subject. Then, the binarizing section 41 binarizes the lung CT image thus cut out. Specifically, the binarizing section 41 also functions as a region extracting section (not illustrated). A region corresponding to a lung of a subject can be cut out from a chest CT image by a publicly known image processing method in which a low X-ray absorption rate of a lung is employed. Note that the control section 4 can be configured to include a region extracting section that is provided separately from the binarizing section 41. The region extracting section cuts out, as a lung CT image, a region corresponding to a lung of a subject, and then supplies, to the binarizing section 41, the lung CT image cut out.

FIG. 1 illustrates a configuration in which the binarizing section 41 fetches a chest CT image from the storage section 3. Note, however, that a configuration of an aspect of the present invention is not limited to such a configuration. For example, an aspect of the present invention can be configured such that a chest CT image obtained by the image obtaining section 2 and to be analyzed is supplied to the binarizing section 41 without being stored in the storage section 3.

The binarizing section 41 binarizes a CT image such that (i) white color is displayed by a pixel having a CT value greater than a binarization reference value and (ii) black color is displayed by a pixel having a CT value equal to or smaller than the binarization reference value. In this case, the binarizing section 41 generates a plurality of binarized images by binarizing, every time the binarizing section 41 changes the binarization reference value, a single CT image obtained by capturing an image of a lung. That is, the binarizing section 41 generates, with respect to a lung CT image, a plurality of binarized images having respective binarization reference values different from each other.

The Betti number calculating section 42 calculates, with respect to each of the plurality of binarized images generated by the binarizing section 41, (1) the number of connected regions that are included in each of the plurality of binarized images and each of which is obtained by connecting pixels each having a pixel value, obtained by binarization, of 0 and (2) the number of case-shaped regions that are included in each of the plurality of binarized images and each of which is surrounded by the pixels each having a pixel value, obtained by binarization, of 0. That is, the Betti number calculating section 42 calculates a zero-dimensional Betti number and a one-dimensional Betti number for a figure of a structure which figure is included in each of the plurality of binarized images.

The connected regions are each a region in which pixels each having a pixel value of 0 have gathered while being adjacent to each other. The connected regions are each surrounded by pixels each having a pixel value of 1 and are independent of each other.

The holes are each an opening that has, as its outer edge, at least part of an outer edge of at least one constituent (in a case of a single constituent, an entire outer edge of such a single constituent). In other words, the holes each surrounded by an outer edge of a constituent include (i) a hole that a single constituent has therein and (ii) a hole that is surrounded by respective portions of outer edges of a plurality of constituents connected to each other.

An existing program can be employed as the Betti number calculating section 42. Examples of the existing program include CHomP. The CHomP is freeware in compliance with a general public license (GNU), and is available from a web site (http://chomp.rutgers.edu/). The existing program is not limited to CHomP. Note, however, that any program other than the CHomP can be employed, provided that a zero-dimensional Betti number and a one-dimensional Betti number can be calculated from an image.

The pattern specifying section 43 specifies at least one of (i) a pattern of a change in zero-dimensional Betti number in accordance with a binarization reference value (a first pattern) and (ii) a pattern of a change in one-dimensional Betti number in accordance with the binarization reference value (a second pattern). For example, the pattern specifying section 43 makes a graph obtained by plotting, with respect to a binarization reference value, at least one of a zero-dimensional Betti number and a one-dimensional Betti number each of which is calculated in a binarized image generated by setting the binarization reference value. In this case, a graph made with respect to a change in zero-dimensional Betti number shows the first pattern, and a graph made with respect to a change in one-dimensional Betti number shows the second pattern.

Note that the pattern specifying section 43 can specify a function that approximately expresses each of (i) a change in zero-dimensional Betti number which change is caused by a change in binarization reference value and (ii) a change in one-dimensional Betti number which change is caused by a change in binarization reference value. In this case, the pattern specifying section 43 can output, for example, a coefficient of a specified function in a form of each of a pattern of a change in zero-dimensional Betti number and a pattern of a change in one-dimensional Betti number. Note, here, that a function (approximate function) that approximately expresses each of a change in zero-dimensional Betti number and a change in one-dimensional Betti number can be a function that can be represented by any relational expression. For example, the approximate function can be an n-th degree function (n is equal to or greater than 1) (including linear approximation and log approximation), an exponential function (power approximation), a trigonometric function, or the like.

The prediction score determining section 44 makes a comparison between (a) the first pattern specified by the pattern specifying section 43 and (b) the at least one reference pattern 32 stored in the storage section 3, and then determines, in accordance with a result of the comparison, information on a change having occurred in a lung.

Note here that the at least one reference pattern 32 is a characteristic amount that is generated by a pattern generating section by analyzing, for each visual score, a chest CT image (i) that has been obtained by capturing an image of a subject who was examined by, for example, a doctor in the past and (ii) whose visual score has already been determined. The at least one reference pattern 32 is generated by learning carried out in step S1 of FIG. 2. Specifically, the at least one reference pattern 32 is graphs made by the pattern specifying section 43 and obtained by plotting a change in zero-dimensional Betti number in accordance with a binarization reference value and a change in one-dimensional Betti number in accordance with a binarization reference value. In a case where a visual score is classified into a plurality of levels, the at least one reference pattern 32 can be generated for the respective plurality of levels.

Specifically, the prediction score determining section 44 compares the first pattern specified by the pattern specifying section 43 with the at least one reference pattern 32 generated for the respective plurality of levels of the visual score, and then determines that a score identical to a score corresponding to one of the at least one reference pattern 32 which one is the most similar to the first pattern is a prediction score.

(Flow of Process of Learning Step S1)

Figure 3:
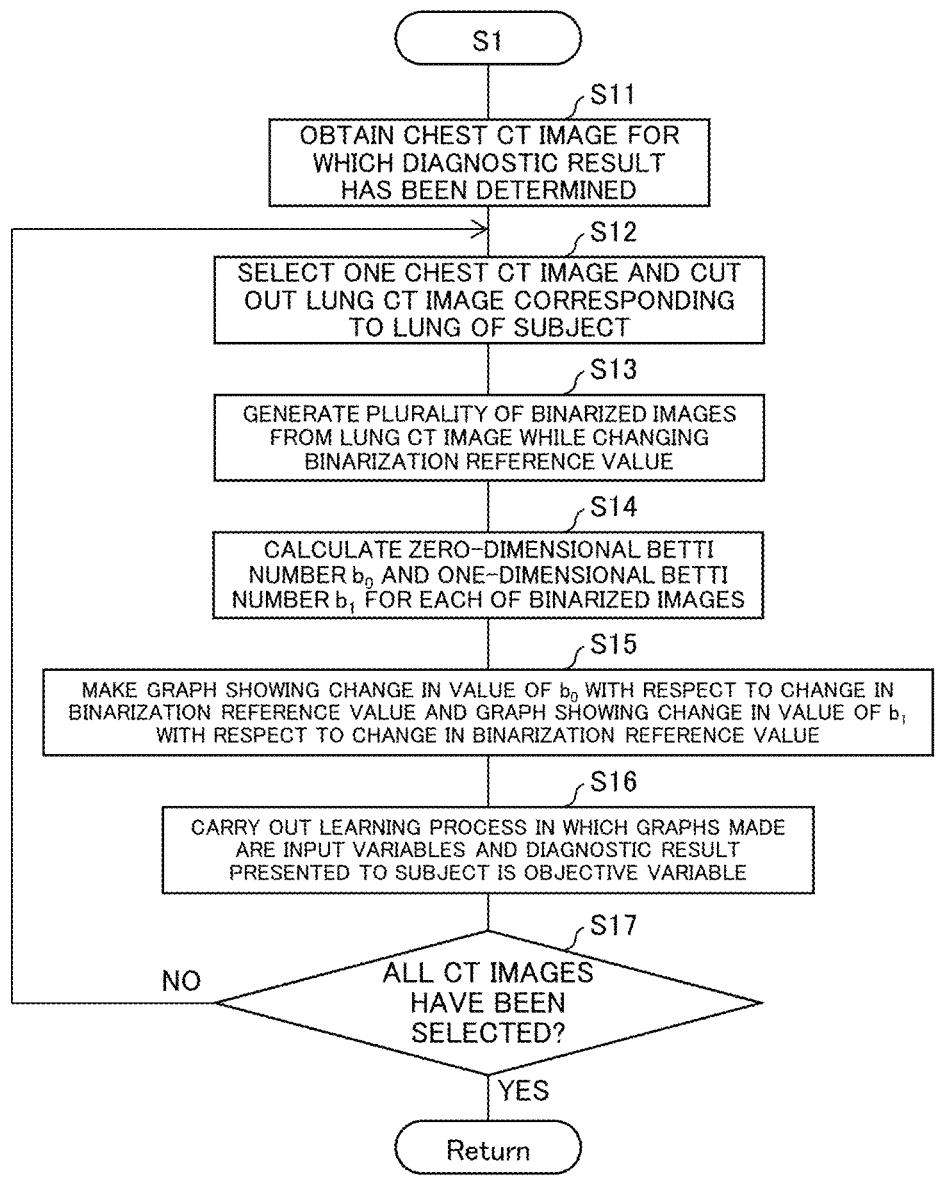
FIG. 3 is a flowchart illustrating an example of a process carried out in step S1 of FIG. 2.
Figure 4:
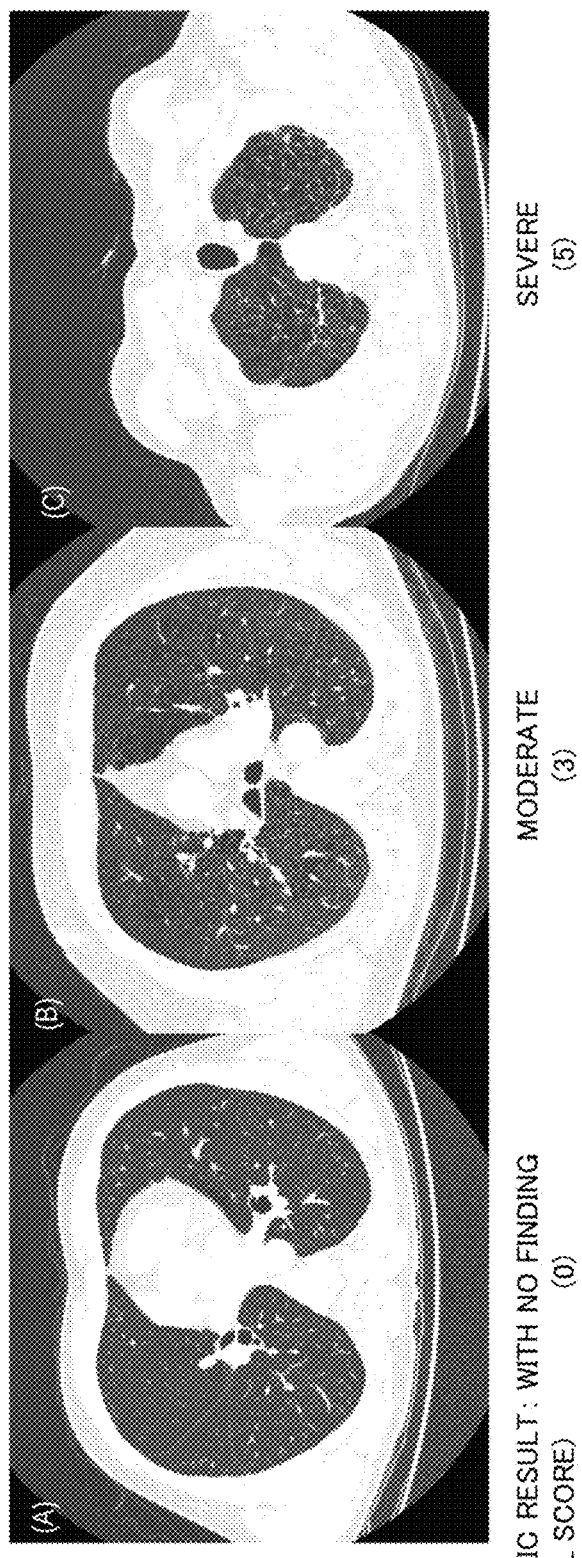
FIG. 4 is a view illustrating examples of chest CT images for use in learning.
Figure 5:
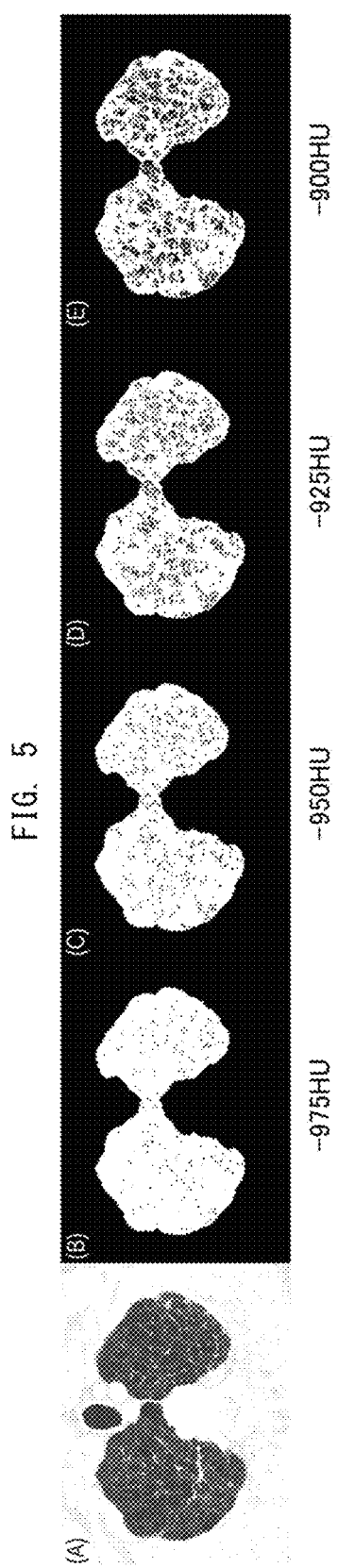
FIG. 5 is a view illustrating examples of binarized images generated with use of different binarization reference values by cutting out a lung CT image from a chest CT image.
Figure 6:
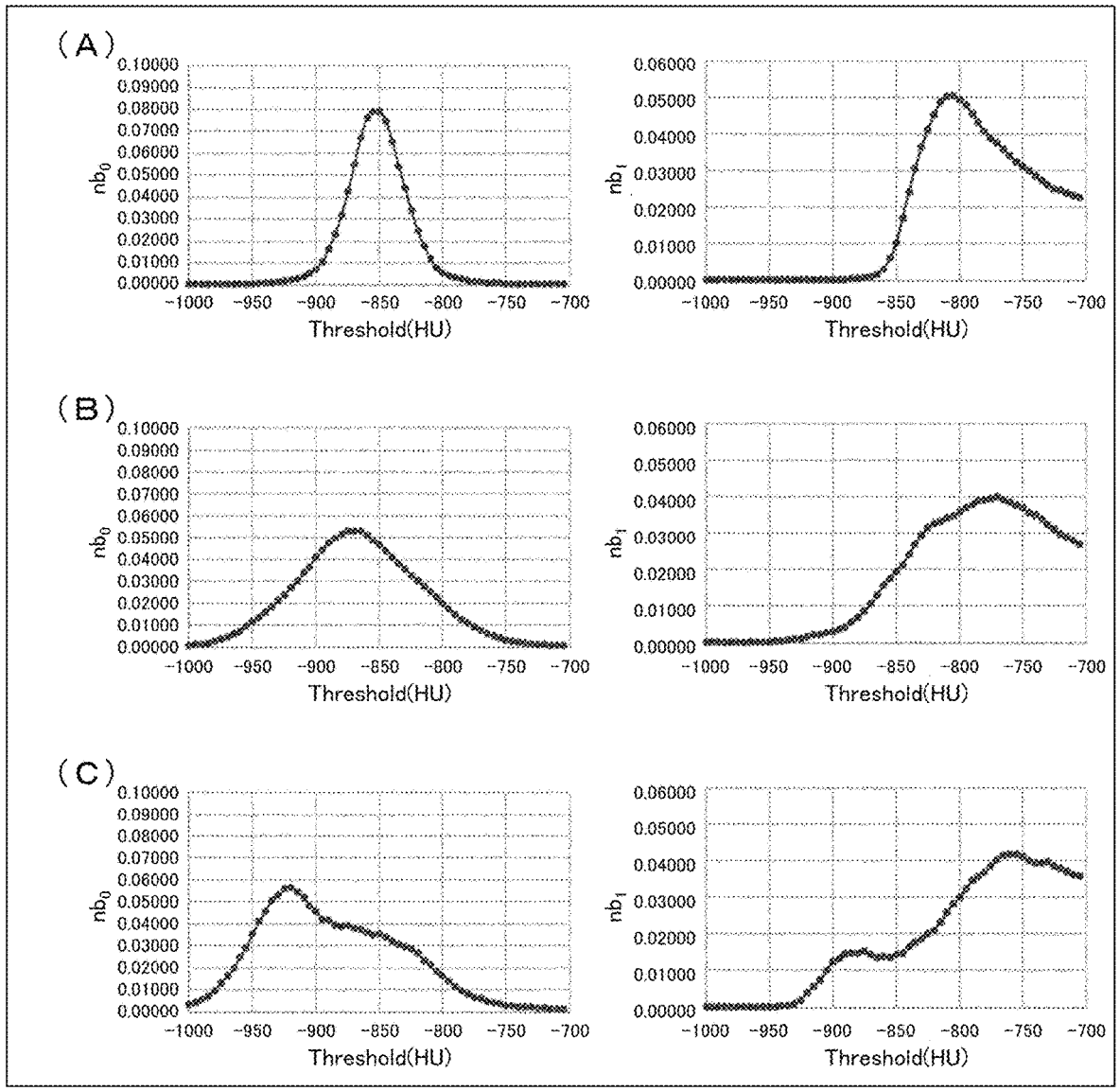
FIG. 6 shows graphs obtained by plotting a change in zero-dimensional Betti number with respect to a binarization reference value and a change in one-dimensional Betti number with respect to a binarization reference value.

Next, while referring to FIGS. 4 to 6, the following description will use FIG. 3 to describe an example of how a process is carried out in step 1 of FIG. 2. FIG. 3 is a flowchart illustrating an example of how a process is carried out in a learning step S1.

The image obtaining section 2 obtains, from the external device 8, a chest CT image for which a diagnostic result such as a visual score has been determined (step S11). The image obtaining section 2 stores, in the storage section 3, the chest CT image thus obtained.

FIG. 4 is a view illustrating examples of chest CT images for use in learning. (A) of FIG. 4 illustrates an example of an image that (i) has no finding showing suspected pulmonary emphysema and (ii) has been diagnosed as showing a normal lung (visual score: 0). (B) of FIG. 4 illustrates an example of an image in which moderate pulmonary emphysema (visual score: 3) has been found. (C) of FIG. 4 illustrates an example of an image in which severe pulmonary emphysema (visual score: 5) has been found.

Next, the learning control section 46 selects one (1) chest CT image from the CT images 31 and send the chest CT image to the binarizing section 41. With the chest CT image, a predetermined visual score is associated. The binarizing section 41 cuts out (extracts) a lung CT image corresponding to a lung (step S12, an extraction step). Furthermore, the binarizing section 41 generates a plurality of binarized images from the lung CT image while changing a binarization reference value with respect to the lung CT image (step S13).

FIG. 5 is a view illustrating examples of binarized images generated with use of different binarization reference values by cutting out a lung CT image from a chest CT image. In order to make a lung region easy to understand, FIG. 5 illustrates images in which black pixels are turned white and vice versa. (A) of FIG. 5 illustrates a chest CT image identical to the chest CT image illustrated in (C) of FIG. 4. (B) to (E) of FIG. 5 illustrate examples of binarized images each generated from the image of (A) of FIG. 5 in a case where a binarization reference value is set to −975 HU to −900 HU.

Next, the Betti number calculating section 42 calculates a zero-dimensional Betti number ($b_0$) and a one-dimensional Betti number ($b_1$) for each of the binarized images (step S14). The pattern specifying section 43 makes (i) a graph showing a relationship between a binarization reference value and a zero-dimensional Betti number and (ii) a graph showing a relationship between a binarization reference value and a one-dimensional Betti number (step S15). That is, the pattern specifying section 43 makes (i) a graph showing a change in value of a zero-dimensional Betti number with respect to a change in binarization reference value and (ii) a graph showing a change in value of a one-dimensional Betti number with respect to a change in binarization reference value.

FIG. 6 shows graphs obtained by plotting a change in zero-dimensional Betti number with respect to a binarization reference value and a change in one-dimensional Betti number with respect to a binarization reference value. The graphs shown on the left side in FIG. 6 are each a graph obtained by plotting (i) a CT value (HU), serving as a binarization reference value (i.e., a value set as a binarization threshold), on a horizontal axis and (ii) a zero-dimensional Betti number on a vertical axis. The graphs shown on the right side in FIG. 6 are each a graph obtained by plotting (i) a CT value (HU), serving as a binarization reference value, on a horizontal axis and (ii) a one-dimensional Betti number on a vertical axis. (A) to (C) of FIG. 6 are graphs made with respect to binarized images generated from the chest CT images illustrated in respective (A) to (C) of FIG. 4. In the graphs of FIG. 6, a value obtained by normalizing a value of a zero-dimensional Betti number or a one-dimensional Betti number by a total pixel number of a lung region is plotted on the vertical axis. Note, however, that graphs of FIG. 6 are not limited to the above graphs. For example, in a case where it is possible to obtain a similar learning effect without normalization of a value of a zero-dimensional Betti number or a one-dimensional Betti number by a total pixel number of a lung region, the normalization is not an essential process. Note that the inventors of the present invention have confirmed that it is possible to increase prediction accuracy in learning by not carrying out the normalization on purpose.

The learning control section 46 (i) obtains, from the pattern specifying section 43, the graphs thus made and (ii) sends, to the prediction score determining section 44, the graphs together with the diagnostic result (e.g., a visual score) that has been associated with the chest CT image. The learning control section 46 causes the prediction score determining section 44 to carry out learning in which it is assumed that the graphs are input variables and the visual score is an objective variable (step S16). Note that an algorithm for use in any machine learning is applicable to an algorithm for such learning. Examples of such an algorithm include "a random forest".

As shown in the six graphs illustrated in FIG. 6, a pattern of a change in value of a zero-dimensional Betti number or a one-dimensional Betti number in accordance with a binarization reference value (i.e., a morphological characteristic of a graph) differs depending on the severity of pulmonary emphysema. For example, it is understood that a binarization reference value that gives a local maximum in a graph of a zero-dimensional Betti number tends to decrease as pulmonary emphysema increases in severity. In contrast, it is understood that a peak width in a graph tends to increase as pulmonary emphysema increases in severity. It is also understood that an inflection point tends to appear in a graph as pulmonary emphysema increases in severity. The learning control section 46 causes the prediction score determining section 44 to carry out learning in which it is assumed that such a characteristic of a graph is an input variable and a visual score is an objective variable.

The learning control section 46 repeats step S12 to step S16 until all CT images 31 stored for learning are selected (step S17). In a case where the prediction score determining section 44 finishes carrying out learning with respect to all the CT images 31, the learning control section 46 (i) assumes that the graphs that have been made by the pattern specifying section 43 are graphs of the at least one reference pattern and (ii) stores the graphs in the at least one reference pattern 32 in accordance with to which visual score the at least one reference pattern 32 corresponds.

(Flow of Process for Determining Prediction Score)

Figure 7:
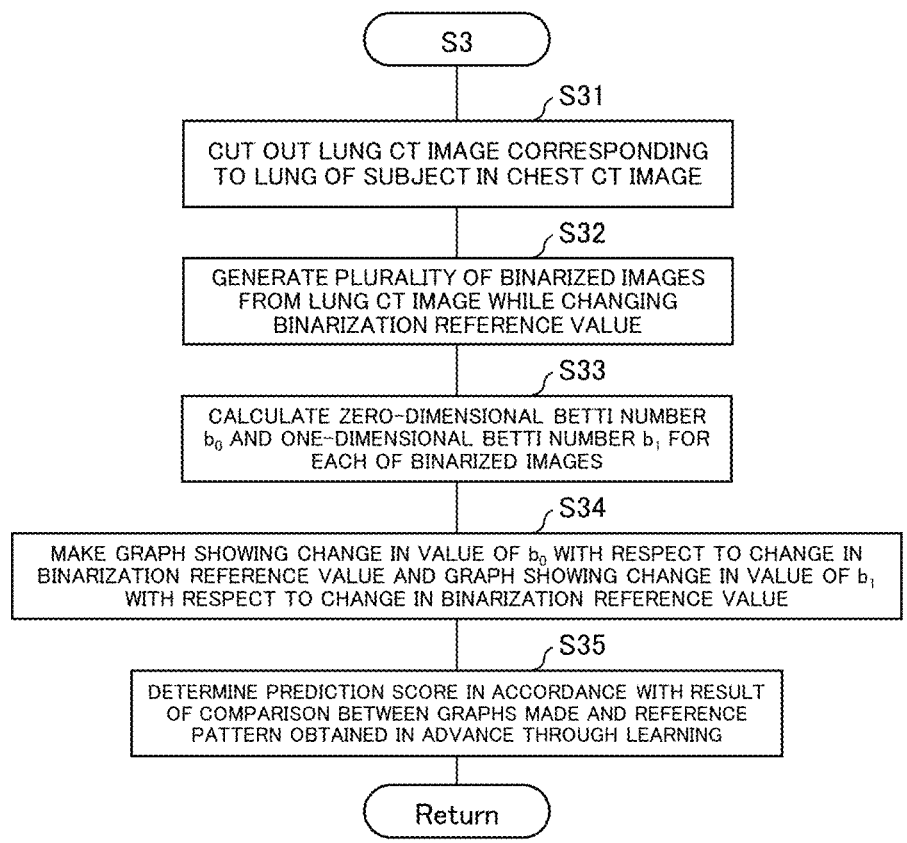
FIG. 7 is a flowchart illustrating an example of how a process for determining a prediction score from a chest CT image to be analyzed is carried out.

Subsequently, the following description will discuss, with reference to FIG. 7, an example of how a process of step S3 of FIG. 2 is carried out. FIG. 7 is a flowchart illustrating an example of how a process for determining a prediction score from a chest CT image to be analyzed is carried out.

In step S31, the binarizing section 41 obtains one (1) chest CT image from the storage section 3 and cuts out a lung CT image corresponding to a lung of a subject (step S31). Furthermore, the binarizing section 41 generates a plurality of binarized images from the lung CT image while changing a binarization reference value with respect to the lung CT image (step S32: a binarizing step).

Subsequently, the Betti number calculating section 42 calculates a zero-dimensional Betti number ($b_0$) and a one-dimensional Betti number ($b_1$) for each of the binarized images (step S33: a calculation step). The pattern specifying section 43 makes graphs obtained by plotting a change in zero-dimensional Betti number in accordance with a binarization reference value and a change in one-dimensional Betti number in accordance with a binarization reference value (step S34).

The prediction score determining section 44 (i) makes a comparison between (a) the graphs that have been made by the pattern specifying section 43 and (b) graphs of the at least one reference pattern 32 which graphs have been obtained, through learning in advance, by plotting a change in zero-dimensional Betti number and a change in one-dimensional Betti number and (ii) determines a prediction score in accordance with a result of the comparison. For example, by comparing (a) the graphs that have been made by the pattern specifying section 43 and (b) the graphs of the at least one reference pattern 32 in terms of, for example, a binarization reference value that gives a local maximum in a graph, a peak width in a graph, and presence and a position of an inflection point in a graph, the prediction score determining section 44 determines that a visual score that is associated with a graph of a reference pattern 32 which graph is the most similar in characteristic to a graph that has been made by the pattern specifying section 43 is a prediction score (step S35: a determination step).

A doctor, for example determines presence and the severity of a disease such as pulmonary emphysema in accordance with a captured image (e.g., a CT image), obtained by capturing an image of a lung, by using, as keys, the following characteristics: (1) In mild pulmonary emphysema, low-attenuation lung areas each having a diameter of approximately 1 cm or so are found to be scattered. (2) In severe pulmonary emphysema, low-attenuation areas are fused to increase, whereas a normal lung region decreases.

The methods illustrated in FIGS. 2 and 7 make it possible to highly accurately determine information on presence and a degree of a change having occurred in a structure. For example, by presenting, to a doctor, the information thus determined, it is possible to appropriately support determination of presence and a degree of a change having occurred in a structure.

Embodiment 2

The following description will specifically discuss another embodiment of the present invention. Note that for convenience, members having functions identical to those of the respective members described in Embodiment 1 are given respective identical reference numerals, and a description of those members is omitted.

(Configuration of Image Analyzing Device 1a)

Figure 8:
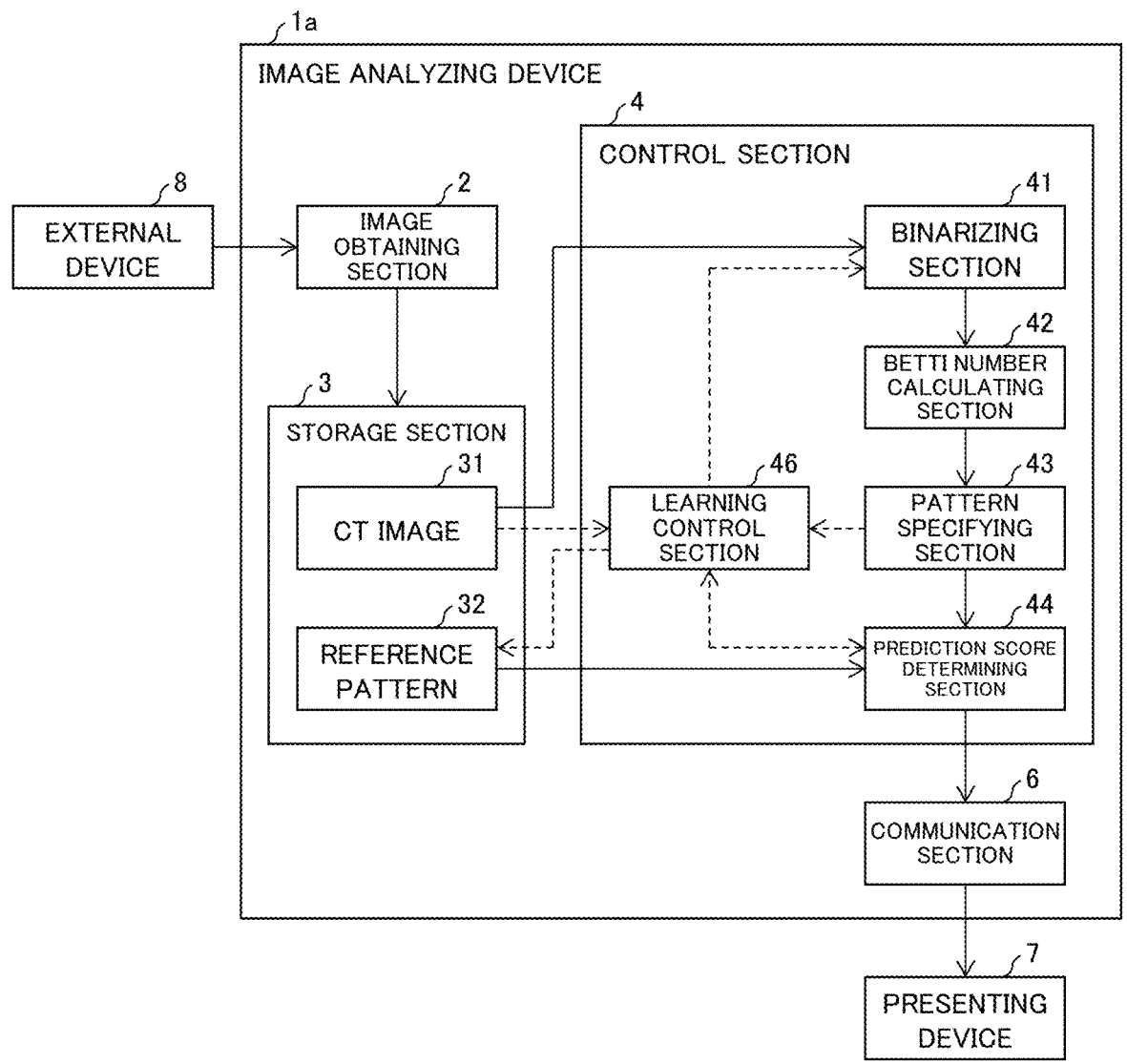
FIG. 8 is a functional block diagram illustrating a configuration example of an image analyzing device in accordance with Embodiment 2 of the present invention.

Next, the following description will discuss a configuration of an image analyzing device 1a with reference to FIG. 8. FIG. 8 is a block diagram illustrating a configuration example of the image analyzing device 1a in accordance with Embodiment 2 of the present invention. The image analyzing device 1a differs from the image analyzing device 1 in that the image analyzing device 1a includes a communication section 6. The communication section 6 (i) obtains, from a prediction score determining section 44, a prediction score that has been determined in accordance with a result of an analysis of a captured image indicated by image data received from an external device 8 and (ii) transmits the prediction score to a presenting device 7.

Note that the image analyzing device 1a can include (i) a plurality of external devices 8 instead of a single external device 8 and (ii) a plurality of presenting devices 7 instead of a single presenting device 7.

(Image Analyzing System)

Figures 9, 10:
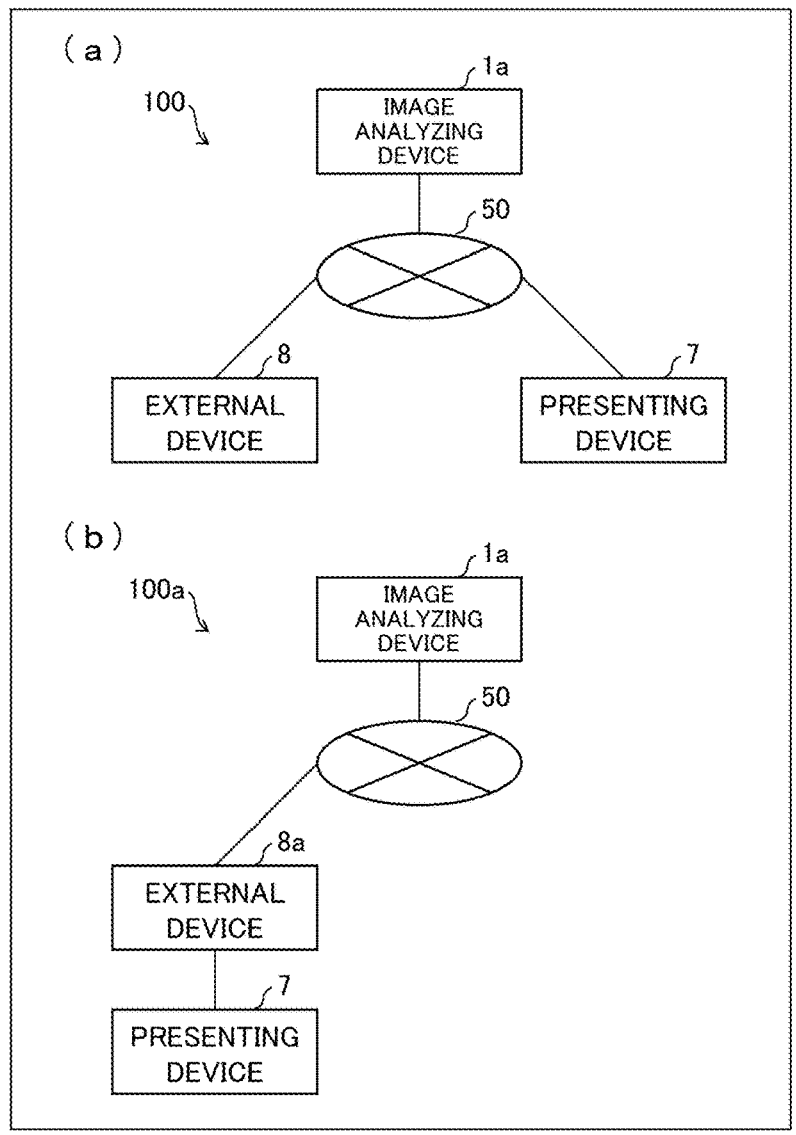
FIG. 9 is a view schematically illustrating configuration examples of image analyzing systems each including an image analyzing device in accordance with an example of the present invention.
FIG. 10 is a table in which (i) an accuracy with which a lung cancer patient was assessed by applying an image analyzing method in accordance with an aspect of the present invention to a chest CT image and (ii) accuracies of other prediction methods to which other indexes are applied are compared.

The following description will discuss, with reference to FIG. 9, configuration examples of image analyzing systems 100 and 100a each including an image analyzing device 1a. FIG. 9 is a view schematically illustrating the configuration examples of the image analyzing systems 100 and 100a each including the image analyzing device 1a in accordance with Embodiment 2 of the present invention. (a) of FIG. 9 illustrates an example in which an external device 8 is provided separately from a presenting device 7. (b) of FIG. 9 illustrates an example in which the presenting device 7 is connected to an external device 8a.

The image analyzing system 100 includes the external device 8, the image analyzing device 1a, and the presenting device 7. The external device 8, the image analyzing device 1a, and the presenting device 7 are each connected to an information communication network 50 such as the Internet. This allows the external device 8, the image analyzing device 1a, and the presenting device 7 to transmit/receive data to/from each other.

The external device 8 can be, for example, a personal computer connected to a CT device, or can be a server (such as an electronic medical record server or a CT image data server) for integrally managing images each obtained by capturing an image of a structure.

The presenting device 7 can be a device that has a function of presenting, to a user, a result of an image analysis. Examples of the presenting device 7 include a display device that includes a display. Alternatively, the presenting device 7 can be communication terminal equipment (e.g., a tablet terminal) that a medical worker has with him/her.

Image data indicative of a captured image obtained by capturing an image of a structure is transmitted from the external device 8 to the image analyzing device 1a. The image analyzing device 1a that has received the image data (i) analyzes the captured image and (ii) transmits, via the communication section 6 to the presenting device 7, a prediction score that has been determined by the prediction score determining section 44.

The image analyzing system 100a includes the external device 8a, the image analyzing device 1a, and the presenting device 7. The external device 8a and the image analyzing device 1a are each connected to the information communication network 50 such as the Internet. This allows the external device 8a and the image analyzing device 1a to transmit/receive data to/from each other. The presenting device 7 is connected to the external device 8a.

That is, the image analyzing device 1a is capable of (i) receiving, from the external device 8 or 8a, an image captured at a distant place, (ii) carrying out an analysis with respect to the image, and then (iii) transmitting, to the presenting device 7, a prediction score, which is a result of the analysis. Note that it is possible to transmit, to the presenting device 7, the prediction score that is associated with a CT image that has been used for the analysis. The presenting device 7 can be a device that is connected to the external device 8, or can be alternatively a device that is independent of each of the image analyzing device 1a and the external device 8.

The image analyzing systems 100 and 100a that are thus configured make it possible to (i) receive a captured image from the respective external devices 8 and 8a, each of which is provided at a distant place, so as to analyze the captured image and (ii) present, to a user at a distant place, the captured image and determined information. Thus, it is also possible to provide a result of a highly accurate image diagnosis to a user at a distant place where no doctor is present or a shortage of doctors is produced.

[Software Implementation Example]

A control block (particularly, the control section 4) of the image analyzing device 1, 1a can be realized by a logic circuit (hardware) provided in an integrated circuit (IC chip) or the like or can be alternatively realized by software.

In the latter case, the image analyzing device 1, 1a includes a computer which executes instructions of a program that is software realizing the foregoing functions. The computer not only includes, for example, at least one processor but also includes a storage medium in which the program is computer-readably recorded. An object of the present invention can be achieved by the processor reading and executing, in the computer, the program stored in the storage medium. Examples of the processor include a central processing unit (CPU). Examples of the storage medium encompass "a non-transitory tangible medium" such as not only a read only memory (ROM) but also a tape, a disk, a card, a semiconductor memory, and a programmable logic circuit. The computer can further include, for example, a random access memory (RAM). The program can be supplied to the computer via any transmission medium (such as a communication network or a broadcast wave) which allows the program to be transmitted. Note that an aspect of the present invention can also be achieved in the form of a computer data signal in which the program is embodied via electronic transmission and which is embedded in a carrier wave.

The present invention is not limited to the embodiments, but can be altered by a skilled person in the art within the scope of the claims. The present invention also encompasses, in its technical scope, any embodiment derived by combining technical means disclosed in differing embodiments.

Example 1

The following description will discuss an Example of the present invention with reference to FIG. 10. FIG. 10 is a table in which (i) an accuracy with which a lung cancer patient was assessed by applying an image analyzing method in accordance with an aspect of the present invention to a chest CT image and (ii) accuracies of other prediction methods to which other indexes are applied are compared.

In FIG. 10, four types of prediction methods are compared. The four types of prediction methods are as follows: (1) a method in which a Brinkman index is used; (2) a method in which a lung region is used as an index; (3) a method in which LAA % is used as an index; and (4) the image analyzing method in accordance with an aspect of the present invention. The Brinkman index is also called a smoking index and is an index obtained by numerically expressing, for example, a smoking history of a patient.

Regarding LAA %, three cases were examined, which are (i) a case where a binarization reference value was set to a CT value of −950 HU, (ii) a case where a binarization reference value was set to a CT value of −910 HU, and (iii) a case where a binarization reference value was set to a CT value of −880 HU.

Regarding the image analyzing method in accordance with an aspect of the present invention, a case was examined where a zero-dimensional Betti number and a one-dimensional Betti number in a binarized image generated by setting a binarization reference value to a CT value of −880 HU were used as indexes. According to the image analyzing method in accordance with an aspect of the present invention, not a pattern of a change in zero-dimensional Betti number in accordance with a binarization reference value and a pattern of a change in one-dimensional Betti number in accordance with a binarization reference value but values of a zero-dimensional Betti number and a one-dimensional Betti number in a binarized image generated by setting a binarization reference value to a predetermined value can be employed as indexes.

As illustrated in FIG. 10, it is revealed that in prediction of presence of lung cancer, prediction carried out by using a zero-dimensional Betti number and a one-dimensional Betti number as indexes is more accurate than any other prediction method and is the most reliable prediction method.

Example 2

FIG. 10 shows a result obtained in a case where presence of lung cancer was predicted with use of a single index. Note, however, it is considered effective to assess a risk of lung cancer by combining indexes (in FIG. 11, written as "PREDICTOR VARIABLE" such as an age, a sex, and a Brinkman index (see Non-patent Literature 1).

In view of this, FIG. 11 shows a result obtained in a case where a plurality of indexes were combined to assess a risk of lung cancer. FIG. 11 is a table showing a result of comparison between accuracies in prediction of lung cancer in (1) a prediction model in which basic indexes that are an age, a sex, and a smoking history (Brinkman index) were used, (2) a prediction model in which LAA % in addition to the basic indexes was used as an index, and (3) a prediction model in which a Betti number in addition to the basic indexes was used as an index.

As illustrated in FIG. 11, no improvement in accuracy with which to assess a risk of lung cancer was found in the prediction model in which LAA % in addition to an age, a sex, and a Brinkman index was used as an index. In contrast, a significant improvement in accuracy with which to assess a risk of lung cancer was found in the prediction model in which a Betti number (here, a one-dimensional Betti number in a binarized image generated by setting a binarization reference value to a CT value of −880 HU was used) in addition to an age, a sex, and a Brinkman index was used as an index. In the example illustrated in FIG. 11, Akaike's Information Criterion (AIC) was used to compare accuracies with which to assess a risk of lung cancer in the above prediction models (1) to (3). Note here that a lower value of AIC means a more accurate prediction model. Furthermore, a difference in AIC by 1.5 to 2 or so is treated as a statistically significant difference. In the prediction model in which only the basic indexes were used, AIC was 785.9. In the prediction model in which LAA % in addition to the basic indexes was used as an index, AIC was 786.2, and no effect was obtained from addition of LAA % to the indexes. In contrast, in the prediction model in which a one-dimensional Betti number $b_1$ in addition to the basic indexes was used as an index, AIC was 779.8, which is lower by 6.1 than the AIC obtained in a case where in which only the basic indexes were used. That is, it is revealed that the prediction model in which a Betti number in addition to an age, a sex, and a Brinkman index was used as an index is lower in AIC than any other prediction model and is the most accurate prediction model as a prediction model for an assessment of a risk of lung cancer.

In general, a pulmonary nodule that serves as a primary lesion is found in a lung CT image in most cases of lung cancer. Examples of the present invention reveal that it is possible to assess a risk of lung cancer without depending on presence of a pulmonary nodule that serves as a candidate for lung cancer. That is, an Example of the present invention is expected to be useful for stratification of a lung cancer risk, irrespective of presence of a pulmonary nodule.

Aspects of the present invention can also be expressed as follows:

An image analyzing method in accordance with an aspect of the present invention is a method for analyzing a captured image obtained by capturing an image of a structure, the image analyzing method including: a binarizing step (S32) of generating, from the captured image, a plurality of binarized images having respective binarization reference values different from each other; a calculation step (S33) of calculating, for each of the plurality of binarized images, a first characteristic numerical value indicative of the number of connected regions each of which is obtained by connecting pixels each having one of pixel values obtained by binarization; and a determination step (S35) of determining, in accordance with a result of a comparison, information on a change having occurred in the structure, the comparison having been made between (i) a first pattern indicative of a relationship between (a) the respective binarization reference values and (b) the first characteristic numerical value and (ii) a predetermined reference pattern.

With the configuration, a plurality of binarized images having respective binarization reference values different from each other are generated with respect to a captured image obtained by capturing an image of a subject, and information on a change having occurred in a structure is determined in accordance with a comparison between (i) a first pattern indicative of a relationship between (a) the respective binarization reference values and (b) the number of connected regions each of which is obtained by connecting pixels each having one of pixel values obtained by binarization and (ii) a predetermined reference pattern.

The term "connected regions" means connected components shown in a captured image, which is a two-dimensional plane. The number of connected regions can be calculated by a process for finding a zero-dimensional Betti number, as a first characteristic numerical value, for each of the plurality of binarized images. Note that a program for calculating a Betti number from an image is publicly known, and a device for executing the program can be used as a calculation section.

The term "structure" means a structural unit in which one or more kinds of constituents have gathered in a certain pattern. Examples of a "structure" include an organ, which is a living body tissue constituted by a collection of, for example, cells.

In carrying out an examination and a diagnosis with use of a captured image obtained by capturing an image of a structure, it is used (i) whether there is a finding that a change having occurred in the structure is different from a normal structure and (ii) to what degree the change having occurred in the structure is different from the normal structure. In order to automate an image diagnosis, it is important how to accurately detect and quantify a characteristic serving as a key to an assessment of a degree of a change having occurred in the structure.

A doctor, for example determines presence and the severity of a disease such as pulmonary emphysema in accordance with a captured image (e.g., a CT image), obtained by capturing an image of a lung, by using, as keys, the following characteristics: (1) In mild pulmonary emphysema, low-attenuation lung areas each having a diameter of approximately 1 cm or so are found to be scattered. (2) In severe pulmonary emphysema, low-attenuation areas are fused to increase, whereas a normal lung region decreases.

By employing the method, the inventors of the present invention (i) detected, from a structure image, a characteristic indicated by a change having occurred in a structure, such as the above (1) and (2) and (ii) quantified the characteristic. Then, the inventors of the present invention found that there is a possibility of being able to assess a degree of the change with high accuracy.

By employing the method, it is possible to highly accurately determine, in accordance with a characteristic that matches a characteristic of a change having occurred in a structure, information on presence and a degree of the change. For example, by presenting, to a doctor, the information thus determined, it is possible to appropriately support determination of presence and a degree of a change having occurred in a structure.

The image analyzing method in accordance with an aspect of the present invention can be configured such that for each of the plurality of binarized images generated in the binarizing step, a second characteristic numerical value is calculated, the second characteristic numerical value indicating the number of case-shaped regions each of which (i) is surrounded by the pixels each having the one of the pixel values and (ii) is composed of pixels each having the other one of the pixel values, and in the determination step, the information on the change having occurred in the structure is determined in accordance with the result of the comparison having been made between (a) a second pattern in which the second characteristic numerical value changes in accordance with a change in binarization reference value and (b) the predetermined reference pattern.

Characteristics of a change having occurred in a structure are diverse, and characteristics exhibited in a captured image are also diverse. Thus, there is a case where it is more appropriate to detect that a change having occurred in a structure is a change in number of case-shaped regions than to detect that a change having occurred in a structure is a change in number of connected regions.

With the configuration, a plurality of binarized images having respective binarization reference values different from each other are generated with respect to a captured image obtained by capturing an image of a subject, and information on a change having occurred in a structure is determined in accordance with a comparison between (i) a pattern in which the number of case-shaped regions each of which is surrounded by the pixels each having the one of the pixel values changes and (ii) a predetermined reference pattern. This allows highly accurate detection and quantification, in a captured image, which is a two-dimensional plane, of various changes having occurred in a structure. Thus, the configuration is applicable to a captured image obtained by capturing an image of changes having occurred in diverse structures.

The term "hole-shaped regions" means spaces (holes) shown in a captured image, which is a two-dimensional plane. The number of hole-shaped regions can be calculated by a process for finding a one-dimensional Betti number, as a second characteristic numerical value, for each of the plurality of binarized images. Note that a program for calculating a Betti number from an image is publicly known as described earlier, and a device for executing the program can be used as a calculation section.

An image analyzing method in accordance with an aspect of the present invention can be configured to further include a learning step (S1) of (i) obtaining the captured image with which determined information on the change having occurred in the structure is associated in advance and (ii) generating the predetermined reference pattern through machine learning carried out with use of learning data including a combination of (a) the first pattern of the captured image and (b) the determined information.

The term "determined information" means information, assessed and determined by a doctor in advance, on a change having occurred in a structure. Examples of the determined information include information indicative of, for example, presence and the severity of a disease having developed in a structure.

With the configuration, a correlation between (a) the first pattern of the captured image with which first pattern determined information on the structure is associated in advance and (b) the determined information is learned. This makes it possible to follow the learned correlation so as to determine, from the first pattern of the captured image to be analyzed, information on the change having occurred in the structure.

The image analyzing method in accordance with an aspect of the present invention can be configured such that the determined information includes information by which to classify, into a plurality of levels, a degree of the change having occurred in the structure, the predetermined reference pattern is generated for each of the plurality of levels, and it is determined in the determination step to which of the plurality of levels the change having occurred in the structure corresponds.

This makes it possible to follow the learned correlation so as to determine, from the first pattern of the captured image to be analyzed, a degree of the change having occurred in the structure.

An image analyzing method in accordance with an aspect of the present invention can be configured to further include an extraction step of extracting, from the captured image, a region corresponding to a structure to be analyzed.

An image obtained by capturing an image of a structure may include a region corresponding to a region that is not to be analyzed. With the configuration, it is possible to extract a region that (i) is an unnecessary region not corresponding to a structure to be analyzed and (ii) may prevent detection and quantification of a change having occurred in a structure.

An image analyzing device (1, 1a) in accordance with an aspect of the present invention is an image analyzing device for analyzing a captured image obtained by capturing an image of a structure, the image analyzing device including: a binarizing section (41) configured to generate, from the captured image, a plurality of binarized images having respective binarization reference values different from each other; a calculation section (Betti number calculating section 42) configured to calculate, for each of the plurality of binarized images, a first characteristic numerical value indicative of the number of connected regions each of which is obtained by connecting pixels each having one of pixel values obtained by binarization; a comparison section (pattern specifying section 43) configured to make a comparison between (i) a first pattern indicative of a relationship between (a) the respective binarization reference values and (b) the first characteristic numerical value and (ii) a predetermined reference pattern; and a determination section (prediction score determining section 44) configured to determine, in accordance with a result of the comparison, information on a change having occurred in the structure.

The configuration brings about an effect, similar to that brought about by the above method, of highly accurately determining, in accordance with a characteristic that matches a characteristic of a change having occurred in a structure, information on presence and a degree of the change.

The image analyzing device in accordance with an aspect of the present invention can be configured such that the calculation section calculates, for each of the plurality of binarized images generated by the binarizing section, a second characteristic numerical value indicative of the number of case-shaped regions each of which (i) is surrounded by the pixels each having the one of the pixel values and (ii) is composed of pixels each having the other one of the pixel values, the comparison section makes the comparison between (a) a second pattern in which the second characteristic numerical value changes in accordance with a change in binarization reference value and (b) the predetermined reference pattern, and the determination section determines, in accordance with the result of the comparison, the information on the change having occurred in the structure.

The configuration allows highly accurate detection and quantification, in a captured image, which is a two-dimensional plane, of various changes having occurred in a structure. Thus, the configuration is applicable to a captured image obtained by capturing an image of diverse structures.

An image analyzing device in accordance with an aspect of the present invention can be configured to further include a learning control section (46) configured to (i) obtain the captured image with which determined information on the change having occurred in the structure is associated in advance and (ii) cause the comparison section to generate the predetermined reference pattern through machine learning carried out with use of learning data including a combination of (a) the first pattern of the captured image and (b) the determined information.

With the configuration, a correlation between (a) the first pattern of the captured image with which first pattern determined information on the structure is associated in advance and (b) the determined information is learned. This makes it possible to follow the learned correlation so as to determine, from the first pattern of the captured image to be analyzed, information on the change having occurred in the structure.

The image analyzing device in accordance with an aspect of the present invention can be configured such that the determined information includes information by which to classify, into a plurality of levels, a degree of the change having occurred in the structure, the predetermined reference pattern is generated for each of the plurality of levels, and the determination section determines to which of the plurality of levels the change having occurred in the structure corresponds.

This makes it possible to determine, from the first pattern of the captured image to be analyzed, a degree of the change having occurred in the structure.

An image analyzing device in accordance with an aspect of the present invention can be configured to further include a region extracting section (binarizing section 41) configured to extract, from the captured image, a region corresponding to a structure to be analyzed.

With the configuration, it is possible to extract a region that (i) is an unnecessary region not corresponding to a structure to be analyzed and (ii) may prevent detection and quantification of a change having occurred in a structure.

An image analyzing system (100, 100a) in accordance with an aspect of the present invention includes: an image analyzing device (1, 1a) recited above; an external device (8, 8a) configured to transmit, to the image analyzing device, image data indicative of a captured image; and a presenting device (7) configured to (i) obtain information determined by the image analyzing device and (ii) present the information.

The configuration makes it possible to (i) receive a captured image obtained with use of, for example, an external device that is provided at a distant place and (ii) analyze the captured image. The configuration also makes it possible to present the captured image and determined information to a user that is present at a distant place.

An image analyzing device in accordance with each aspect can be realized by a computer. In this case, the scope of the present invention also encompasses (i) an image analyzing program for realizing an image analyzing device recited above by a computer by causing the computer to operate as sections (software components) of the image analyzing device and (ii) a recording medium in which the image analyzing program is computer-readably recorded.

REFERENCE SIGNS LIST 1, 1a Image analyzing device
2 Image obtaining section
4 Control section
7 Presenting device
8, 8a External device
41 Binarizing section (region extracting section)
42 Betti number calculating section (calculation section)
43 Pattern specifying section (comparison section)
44 Prediction score determining section (determination section)
46 Learning control section
100, 100a image analyzing system
S1 Learning step
S32 Binarizing step
S33 Calculation step
S35 Determination step

The invention claimed is:

1. An image analyzing method for analyzing a captured image obtained by capturing an image of a structure, said image analyzing method comprising:
a binarizing step of generating, from the captured image, a plurality of binarized images having respective binarization threshold values different from each other;
a calculation step of calculating, for each of the plurality of binarized images, a first characteristic numerical value indicative of the number of connected regions each of which is obtained by connecting pixels each having one of pixel values obtained by binarization; and
a determination step of determining, in accordance with a result of a comparison, information on a change having occurred in the structure, the comparison having been made between
(i) a first pattern indicative of a relationship between (a) the respective binarization threshold values and (b) the first characteristic numerical value and
(ii) a predetermined reference pattern that has been generated by a pattern generating method comprising:
obtaining a reference image for which a diagnostic result has been determined,
generating from the reference image a plurality of binarized images having respective binarization threshold values different from each other,
calculating, for each of the plurality of binarized images, at least one of
a first characteristic numerical value indicative of the number of connected regions each of which is obtained by connecting pixels each having one of pixel values obtained by binarization and
a second characteristic numerical value indicating the number of case-shaped regions each of which (i) is surrounded by the pixels each having the one of the pixel values and (ii) is composed of pixels each having the other one of the pixel values,
generating a reference pattern indicative of a relationship between (a) the respective binarization threshold values and (b) at least one of the first characteristic numerical value and a reference pattern indicative of a relationship between (a) the respective binarization threshold values and (b) the second characteristic numerical value, and
correlating the reference pattern with determined information comprising information, assessed and determined by a doctor in advance, on a change having occurred in a structure of the reference image to provide the predetermined reference pattern.

2. The image analyzing method as set forth in claim 1, wherein
for each of the plurality of binarized images generated in the binarizing step, a second characteristic numerical value is calculated, the second characteristic numerical value indicating the number of case-shaped regions each of which (i) is surrounded by the pixels each having the one of the pixel values and (ii) is composed of pixels each having the other one of the pixel values, and
in the determination step, the information on the change having occurred in the structure is determined in accordance with the result of the comparison having been made between (a) a second pattern in which the second characteristic numerical value changes in accordance with a change in binarization threshold value and (b) the predetermined reference pattern.

3. An image analyzing method as set forth in claim 1, wherein the predetermined reference pattern is generated through machine learning carried out with use of learning data including a combination of (a) the reference pattern and (b) the determined information.

4. The image analyzing method as set forth in claim 3, wherein
the determined information includes information by which to classify, into a plurality of levels, a degree of the change having occurred in the structure,
the predetermined reference pattern is generated for each of the plurality of levels, and
it is determined in the determination step to which of the plurality of levels the change having occurred in the structure corresponds.

5. An image analyzing method as set forth in claim 1, further comprising an extraction step of extracting, from the captured image, a region corresponding to a structure to be analyzed.

6. An image analyzing device for analyzing a captured image obtained by capturing an image of a structure, said image analyzing device comprising a CPU configured to:
generate, from the captured image, a plurality of binarized images having respective binarization threshold values different from each other;
calculate, for each of the plurality of binarized images, a first characteristic numerical value indicative of the number of connected regions each of which is obtained by connecting pixels each having one of pixel values obtained by binarization;
make a comparison between
(i) a first pattern indicative of a relationship between (a) the respective binarization threshold values and (b) the first characteristic numerical value and
(ii) a predetermined reference pattern that has been generated by a pattern generating method comprising:
obtaining a reference image for which a diagnostic result has been determined,
generating from the reference image a plurality of binarized images having respective binarization threshold values different from each other,
calculating, for each of the plurality of binarized images, at least one of
a first characteristic numerical value indicative of the number of connected regions each of which is obtained by connecting pixels each having one of pixel values obtained by binarization and
a second characteristic numerical value indicating the number of case-shaped regions each of which (i) is surrounded by the pixels each having the one of the pixel values and (ii) is composed of pixels each having the other one of the pixel values,
generating a reference pattern indicative of a relationship between (a) the respective binarization threshold values and (b) at least one of the first characteristic numerical value and a reference pattern indicative of a relationship between (a) the respective binarization threshold values and (b) the second characteristic numerical value, and correlating the reference pattern with determined information comprising information, assessed and determined by a doctor in advance, on a change having occurred in a structure of the reference image to provide the predetermined reference pattern; and determine, in accordance with a result of the comparison, information on a change having occurred in the structure.

7. The image analyzing device as set forth in claim 6, wherein the CPU calculates, for each of the plurality of binarized images generated by the binarizing section, a second characteristic numerical value indicative of the number of case-shaped regions each of which (i) is surrounded by the pixels each having the one of the pixel values and (ii) is composed of pixels each having the other one of the pixel values, makes the comparison between (a) a second pattern in which the second characteristic numerical value changes in accordance with a change in binarization threshold value and (b) the predetermined reference pattern, and determines, in accordance with the result of the comparison, the information on the change having occurred in the structure.

8. The image analyzing device as set forth in claim 6, wherein the CPU is further configured to generate the predetermined reference pattern through machine learning carried out with use of learning data including a combination of (a) the reference pattern and (b) the determined information.

9. The image analyzing device as set forth in claim 8, wherein the determined information includes information by which to classify, into a plurality of levels, a degree of the change having occurred in the structure, the predetermined reference pattern is generated for each of the plurality of levels, and the CPU determines to which of the plurality of levels the change having occurred in the structure corresponds.

10. The image analyzing device as set forth in claim 6, wherein the CPU is further configured to extract, from the captured image, a region corresponding to a structure to be analyzed.

11. A computer-readable non-transitory recording medium in which an image analyzing program is stored said image analyzing program being configured:

to generate, from a captured image obtained by capturing an image of a structure, a plurality of binarized images having respective binarization threshold values different from each other;

to calculate, for each of the plurality of binarized images, a first characteristic numerical value indicative of the number of connected regions each of which is obtained by connecting pixels each having one of pixel values obtained by binarization;

to make a comparison between (i) a first pattern indicative of a relationship between (a) the respective binarization threshold values and (b) the first characteristic numerical value and (ii) a predetermined reference pattern that has been generated by a pattern generating method comprising:

obtaining a reference image for which a diagnostic result has been determined, generating from the reference image a plurality of binarized images having respective binarization threshold values different from each other, calculating, for each of the plurality of binarized images, at least one of a first characteristic numerical value indicative of the number of connected regions each of which is obtained by connecting pixels each having one of pixel values obtained by binarization and a second characteristic numerical value indicating the number of case-shaped regions each of which (i) is surrounded by the pixels each having the one of the pixel values and (ii) is composed of pixels each having the other one of the pixel values, generating a reference pattern indicative of a relationship between (a) the respective binarization threshold values and (b) at least one of the first characteristic numerical value and a reference pattern indicative of a relationship between (a) the respective binarization threshold values and (b) the second characteristic numerical value, and correlating the reference pattern with determined information comprising information, assessed and determined by a doctor in advance, on a change having occurred in a structure of the reference image to provide the predetermined reference pattern; and to determine, in accordance with a result of the comparison, information on a change having occurred in the structure.

* * * * *